United States Patent
Rogers et al.

(10) Patent No.: US 11,164,437 B2
(45) Date of Patent: Nov. 2, 2021

(54) SWIMMING POOL MONITORING

(71) Applicant: Alarm.com Incorporated, Tysons, VA (US)

(72) Inventors: Thomas Rogers, Frederick, MD (US); Gary Franklin Bart, Weston, FL (US); Dean Constantine, Ft. Lauderdale, FL (US); John Varn, Tequesta, FL (US)

(73) Assignee: Alarm.com Incorporated, Tysons, VA (US)

( * ) Notice: Subject to any disclaimer, the term of this patent is extended or adjusted under 35 U.S.C. 154(b) by 119 days.

(21) Appl. No.: 16/358,086

(22) Filed: Mar. 19, 2019

(65) Prior Publication Data
US 2019/0287378 A1    Sep. 19, 2019

Related U.S. Application Data

(60) Provisional application No. 62/644,862, filed on Mar. 19, 2018.

(51) Int. Cl.
*G08B 21/18*    (2006.01)
*G01N 33/18*    (2006.01)
(Continued)

(52) U.S. Cl.
CPC ............... *G08B 21/18* (2013.01); *E04H 4/06* (2013.01); *E04H 4/14* (2013.01); *G01N 33/18* (2013.01); *G01S 15/88* (2013.01); *G06K 9/00362* (2013.01); *G06K 9/00771* (2013.01); *G08B 21/08* (2013.01); *H04N 5/23203* (2013.01)

(58) Field of Classification Search
CPC ...... G08B 21/18; G08B 31/00; G08B 21/084; G08B 21/08; G01N 33/18; G06K 9/00771; G06K 9/00362; G06K 9/00342; E04H 4/14; E04H 4/06; H04N 7/188; H04N 5/232;
(Continued)

(56) References Cited

U.S. PATENT DOCUMENTS

| 4,017,842 A | 4/1977 | Vineyard |
| 9,640,058 B1 | 5/2017 | Bollman et al. |

(Continued)

OTHER PUBLICATIONS

PCT International Search Report and Written Opinion in International Application No. PCT/US2019/022978, dated Jun. 14, 2019, 8 pages.

(Continued)

*Primary Examiner* — James J Yang
(74) *Attorney, Agent, or Firm* — Fish & Richardson P.C.

(57) ABSTRACT

A computer implemented method including receiving, by a monitoring system that is configured to monitor a property and from an electronic pool device that is configured to monitor a swimming pool at the property, sensor data, analyzing, by the monitoring system, the sensor data, based on analyzing the sensor data, generating, by the monitoring system, an instruction to activate a camera of the electronic pool device, providing, by the monitoring system to the electronic pool device, the instruction to activate the camera, receiving, by the monitoring system from the electronic pool device, image data, analyzing, by the monitoring system, the image data, based on analyzing the image data, identifying a monitoring system action to perform, and performing the monitoring system action.

19 Claims, 6 Drawing Sheets

(51) Int. Cl.
*G01S 15/88* (2006.01)
*G06K 9/00* (2006.01)
*E04H 4/14* (2006.01)
*H04N 5/232* (2006.01)
*G08B 21/08* (2006.01)
*E04H 4/06* (2006.01)

(58) Field of Classification Search
CPC ...... H04N 7/18; H04N 5/23203; G01S 15/86; G01S 15/523; G01S 15/88
See application file for complete search history.

(56) References Cited

U.S. PATENT DOCUMENTS

| | | | | |
|---|---|---|---|---|
| 9,940,826 | B1* | 4/2018 | Divakara | G08B 29/183 |
| 10,096,219 | B1* | 10/2018 | Maurer | G08B 13/1427 |
| 10,665,073 | B1* | 5/2020 | Richerson, Jr. | H04N 5/2254 |
| 2007/0034249 | A1 | 2/2007 | Romano et al. | |
| 2014/0303757 | A1* | 10/2014 | Pruchniewski | A61H 33/005 |
| | | | | 700/90 |
| 2015/0092055 | A1* | 4/2015 | Scalisi | G08B 21/088 |
| | | | | 348/143 |
| 2015/0112885 | A1* | 4/2015 | Fadell | G08B 25/008 |
| | | | | 705/330 |
| 2016/0044287 | A1 | 2/2016 | Scalisi et al. | |
| 2016/0104359 | A1* | 4/2016 | AlMahmoud | G01S 15/42 |
| | | | | 367/112 |
| 2016/0155314 | A1 | 6/2016 | Snyder | |
| 2016/0189531 | A1 | 6/2016 | Modi et al. | |
| 2017/0098361 | A1 | 4/2017 | Sentosa et al. | |
| 2017/0223314 | A1* | 8/2017 | Collings, III | H04N 5/2259 |
| 2017/0261957 | A1 | 9/2017 | Boettcher et al. | |
| 2017/0365150 | A1* | 12/2017 | Bennett | H04L 63/0428 |
| 2018/0041865 | A1 | 2/2018 | Rabb | |
| 2018/0053401 | A1 | 2/2018 | Martin et al. | |
| 2018/0089980 | A1* | 3/2018 | Snyder | G06K 9/00771 |
| 2018/0112430 | A1* | 4/2018 | Shalon | C02F 1/685 |

OTHER PUBLICATIONS

PCT International Preliminary Report on Patentability in International Application No. PCT/US2019/022978, dated Oct. 1, 2020, 7 pages.

Extended European Search Report in EP Appln. No. 19770338.2, dated Apr. 19, 2021, 8 pages.

* cited by examiner

SWIMMING POOL MONITORING

CROSS REFERENCE TO RELATED APPLICATION

This application claims benefit of U.S. Provisional Application No. 62/644,862 filed Mar. 19, 2018, and titled "Swimming Pool Monitoring Device," which is incorporated by reference in its entirety.

TECHNICAL FIELD

This disclosure relates to property monitoring technology and, for example, the use of an electronic pool device that is configured to monitor a swimming pool at a monitored property.

BACKGROUND

Many people equip homes and businesses with monitoring systems to provide increased security for their homes and businesses.

SUMMARY

Techniques are described for monitoring technology. For example, techniques are described for monitoring a swimming pool at a monitored property using the electronic pool device. The electronic pool device is in communication with a control unit that manages the monitoring system at the monitored property.

According to an innovative aspect of the subject matter described in this application, a monitoring system that is configured to monitor a property, the monitoring system includes an electronic pool device that is configured to monitor a swimming pool located at the property, the electronic pool device including a camera that is configured to capture image data, and a sensor that is configured to generate sensor data, and a monitor control unit. The monitor control unit is configured to receive, from the electronic pool device, the sensor data, analyze the sensor data, based on analyzing the sensor data, generate an instruction to activate the camera of the electronic pool device, provide, to the electronic pool device, the instruction to activate the camera, receive, from the electronic pool device, the image data, analyze the image data, based on analyzing the image data, identify a monitoring system action to perform, and perform the monitoring system action.

These and other implementations each optionally include one or more of the following optional features. The monitor control unit is configured to receive, from a server, weather data that indicates that a wind forecast at the property, based on the wind forecast at the property, adjust a wave height threshold and a wave period threshold, analyze the sensor data by comparing the sensor data that indicates the wave height and the wave period to the wave height threshold and a wave period threshold. The monitor control unit is configured to receive first historical sensor data captured by the electronic pool device and other electronic pool devices during emergency events, receive second historical sensor data captured by the electronic pool device and the other electronic pool devices during non-emergency events, and train, using machine learning, a model that is configured to receive the sensor data and determine whether an emergency event likely exists. The monitor control unit is configured to analyze the sensor data by providing the sensor data as an input to the model that is configured to receive the sensor data and determine whether an emergency event likely exists, and generate an instruction to activate the camera of the electronic pool device based on determining that an emergency event likely exists.

The monitor control unit is configured to receive, from the electronic pool device, the sensor data by receiving motion data, receive, from a server, weather data that indicates the weather conditions at the property, based on receiving, from the server, the weather data that indicates the weather at the property and the motion data, increase a motion threshold, and analyze the sensor data by comparing the motion data to the increased motion threshold. The monitor control unit is configured to receive, from the electronic pool device, the sensor data by receiving motion data, determine that an armed status of the monitoring system is armed away, based on determining that the monitoring system is armed away, increase a motion threshold, and analyze the sensor data by comparing the motion data to the increased motion threshold. The monitor control unit is configured to receive, from the electronic pool device, the sensor data by receiving motion data, determine an armed status of the monitoring system, based on determining that the monitoring system is unarmed, increase a motion threshold, and analyze the sensor data by comparing the motion data to the increased motion threshold.

The monitor control unit is configured to receive, from the electronic pool device, the sensor data by receiving motion data, determine an armed status of the monitoring system, based on determining that the monitoring system is armed stay, decrease a motion threshold, and analyze the sensor data by comparing the motion data to the decreased motion threshold. The monitor control unit is configured to determine that use of the pool is not allowed at a current time, analyze the image data by analyzing the image data using one or more video analytic techniques, based on analyzing the image data using the one or more video analytic techniques, determine that a person is in the pool, based on determining that the person is in the pool at the current time when the use of the pool is not allowed, identify a monitoring system action to perform by identifying the monitoring system action of activating an alarm, and perform the monitoring system action by activating the alarm. The monitor control unit is configured to identify the monitoring system action to perform by identifying the monitoring system action of activating one or more lights in a vicinity of the pool, and perform the monitoring system action by activating the one or more lights in the vicinity of the pool.

The monitor control unit is configured to determine that an object is at the bottom of the pool based on analyzing the image data, based on determining that an object is at the bottom of the pool, identify the monitoring system action to perform by identifying the monitoring system action of communicating a notification to a user device of a resident of the property, and perform the monitoring system action by communicating the notification to the user device of the resident of the property indicating that maintenance is required. The monitor control unit is configured to determine that a person in the pool is in distress based on analyzing the sensor data and the image data, based on determining that the swimmer in the pool is in distress, identify the monitoring system action to perform by identifying the monitoring system action of contacting emergency services, and perform the monitoring system action by contacting emergency services. The monitor control unit is configured to perform the monitoring system action by outputting an audible siren from a speaker in the vicinity of the pool.

The monitor control unit is configured to receive, from the electronic pool device, pH data, wherein the electronic pool device includes a pH sensor that is configured to measure a pH of water in the swimming pool, analyzing the pH data by comparing the pH sensor data to a pH threshold, based on comparing the pH data to the pH threshold, determine that the pH data exceeds the pH threshold, and based on determining that the pH data exceeds the pH threshold, perform a monitoring system action by communicating a notification to the user device of a resident of the property.

The electronic pool device includes a first portion that is located under a pool water surface, the first portion including a camera and one or more sensors, a second portion that is located above the pool water surface, the second portion including one or more motion sensors, and the first portion is connected to the second portion by a flexible tether. The first portion of the electronic pool device that is located under the pool water surface includes a sonar detector.

According to another innovative aspect of the subject matter described in this application, a computer implemented method includes receiving, by a monitoring system that is configured to monitor a property and from an electronic pool device that is configured to monitor a swimming pool at the property, sensor data, analyzing, by the monitoring system, the sensor data, based on analyzing the sensor data, generating, by the monitoring system, an instruction to activate a camera of the electronic pool device, providing, by the monitoring system to the electronic pool device, the instruction to activate the camera, receiving, by the monitoring system from the electronic pool device, image data, analyzing, by the monitoring system, the image data, based on analyzing the image data, identifying a monitoring system action to perform, and performing the monitoring system action.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Pool safety is important regardless of whether a homeowner is at the residence or the residence is vacant. Over the past ten years, there has been an average of over three thousand fatal drownings per year. Many of these drownings were the result of an unattended pool.

Techniques are described for integrating an electronic pool device into a monitoring system to facilitate the monitoring of a swimming pool at a monitored property. The electronic pool device may include a battery powered camera and one or more sensors configured to detect motion in the swimming pool. The electronic pool device may be in communication with a control unit of the monitoring system at the monitored property. The electronic pool device monitors for unexpected activity at the pool. For example, the electronic pool device generates an alert to a user when motion is detected at the pool while the pool is not in use.

Figure 1:
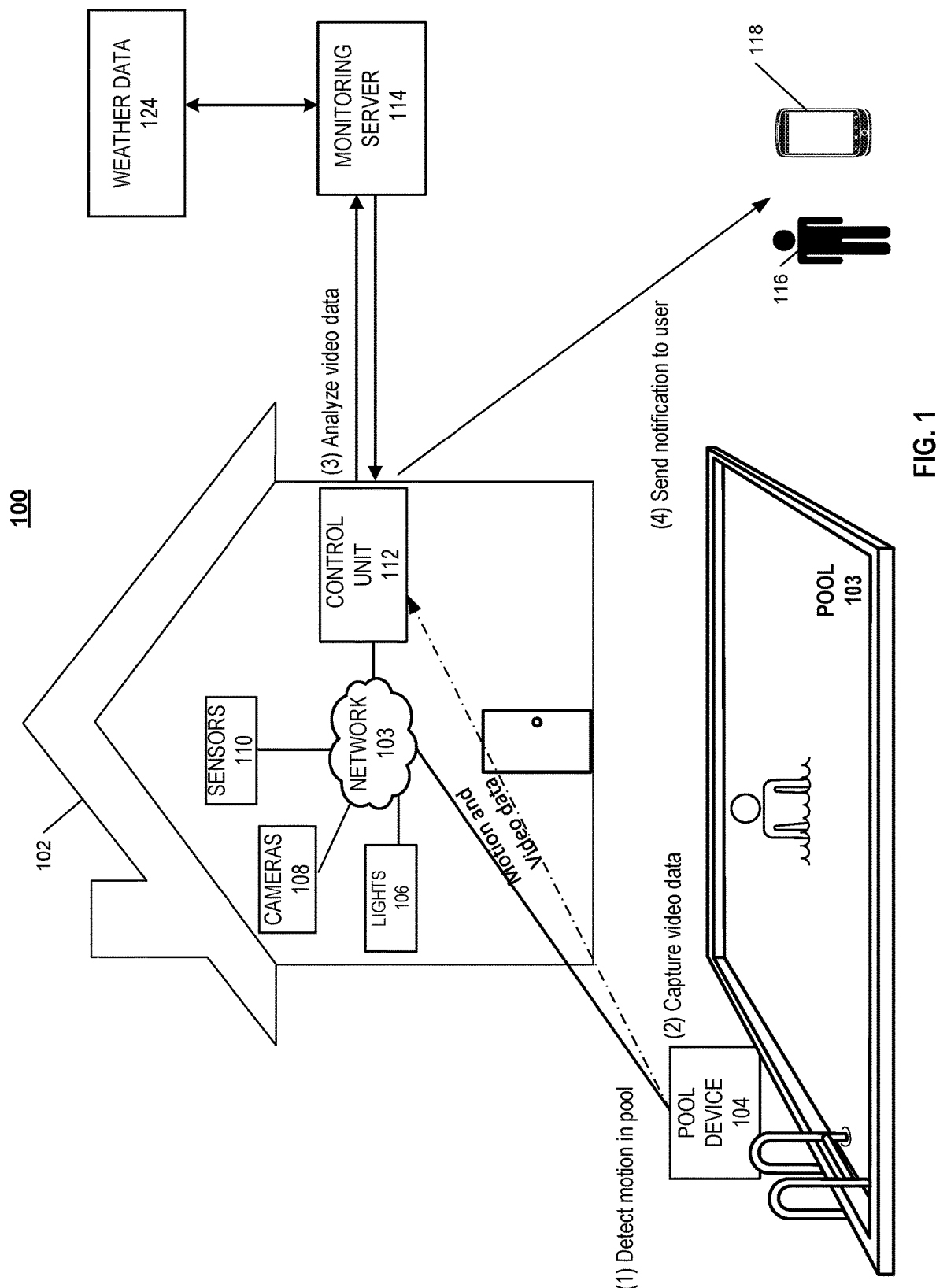
FIG. 1 illustrates an example of a system for detecting motion in a swimming pool.

FIG. 1 illustrates an example of a monitoring system 100 integrated with an electronic pool device. As shown in FIG. 1, a property 102 (e.g. a home) of a user 116 is monitored by an in-home monitoring system (e.g. in-home security system) that includes components that are fixed within the property 102. The in-home monitoring system may include a control unit 112, one or more sensors 110, one or more cameras 108, one or more lights 106, and an electronic pool device 104. Each of the one or more sensors 110, one or more cameras 108, one or more lights 106, and the electronic pool device 104 are in communication with the control unit 112 to form the monitoring ecosystem of the monitored property.

The user may integrate the electronic pool device 104 to monitor the conditions of a swimming pool 103 at the monitored property 102. The swimming pool 103 may be an indoor pool located within the monitored property 102, or an outdoor pool located on the lawn of the monitored property 102. In some examples, the electronic pool device 104 may be used to monitor the conditions of a hot tub. In these examples, the electronic pool device 104 may be configured to detect only motion not caused by the bubbles generated in the hot tub. The electronic pool device 104 also monitors the pool for unexpected movement, for example when a child slips into the pool 103. The electronic pool device 104 may be used to monitor the pool water temperature, the pool water pH levels, and any other suitable status conditions.

The electronic pool device 104 may include a camera portion that is configured to be placed under the surface of the water, and a surface portion that includes an antenna, a microphone and one or more motion detecting sensors. The one or more motion detecting sensors may include an accelerometer, a gyroscope, a mercury switch, or any other appropriate motion detecting sensors. The camera portion and the surface portion of the electronic pool device 104 may each be waterproof. The antenna is configured to allow the electronic pool device 104 to communicate with the control unit 112. In some implementations, the electronic pool device 104 may communicate with the control unit 112 through Bluetooth, Z-Wave, ZigBee, Wi-Fi, or other suitable form of wireless communication.

The camera portion of the electronic pool device 104 includes a rechargeable battery that is charged by the energy generated from the water flowing through the pool's plumbing system. The camera portion of the electronic pool device 104 may be configured to mount to an existing pool jet, and the battery of the camera portion charges as water flows through the pool jet. In some implementations, the camera portion of the electronic pool device 104 may be in communication with a distinct fitting that is mounted to the pool jet or is in communication with a skimmer, or an irrigation system. As the pool water flows through the fitting or the skimmer, the energy generated is transferred to the battery. In some implementations, the camera portion of the electronic pool device 104 may be charged through a solar panel located on the surface portion of the device 104. The camera portion of the electronic pool device 104 is connected to the surface portion of the device by a flexible tether. The tether may be configured to allow the surface portion of the device 104 to float on the surface of the water immediately above the camera portion.

For the example illustrated in FIG. 1, the electronic pool device 104 detects motion in the pool. In some implementations, the electronic pool device 104 is placed in the swimming pool 103 when the pool is not being utilized. In these implementations, when the one or more motion sensors of the surface portion of electronic pool device 104 detect motion in the pool, the motion is considered as unexpected motion, and may trigger an alarm or some other form of notification to be generated. For example, the electronic pool device 104 may be placed in the pool 103 when an adult user does not expect any users in the pool 103.

The one or more motion sensors of the surface portion of the electronic device 104 communicate the motion data to the control unit 112. The control unit 112 compares the motion data to a motion threshold. The motion threshold may be a threshold determined by the control unit 112 based on the weather conditions at the location of the monitored property 102. The control unit 112 at the monitored property 102 may receive weather data from a weather data server 124. In some examples, the weather data server 124 is in direct communication with the control unit 112. In other examples, the weather data server 124 communicates with a monitoring server 114 which in turn communicates with the control unit 112. The control unit 112 may adjust the motion threshold based on the weather data indicating windy or rainy conditions.

The control unit 112 may adjust the motion threshold based on the time of the day. For example, the control unit may increase the motion threshold during the weekday between the hours of 8:00 am and 3:00 pm when the residents of the property 102 are away from the home. In these examples, the control unit 112 increases the motion threshold to ensure only motion caused by a person entering the pool triggers an alarm or a notification to be generated. The control unit may decrease the motion threshold during the weekday evening hours and the weekend when the residents of the property 102 are more likely to be at the property. In these examples, the control unit 112 decreases the motion threshold to ensure that any motion detected generates a notification to the resident. The control unit 112 may adjust the motion threshold based on the armed status of the property 102. For example, when the monitoring system at the monitored property 102 is armed away, the system assumes that the residents of the property are away and the control unit increases the motion threshold. For another example, when the monitoring system is armed stay, the system assumes that the residents of the property are at the property and the control unit decreases the motion threshold.

In some implementations, when the motion detected by the one or more motion detection sensors exceeds the motion threshold, the control unit 112 generates a notification. The user 116 may set one or more rules for the types of notifications generated by the control unit 112. The user 116 may log into a monitoring system application that runs on the user device 118 and that is managed by the control unit 112. For example, the user may set preferences to receive a notification on the user device 118 when the pool device 104 detects motion. The user may configure their preferences to receive one or more different notifications based on one or more different thresholds. For example, the user may set their preferences to receive a notification when a first motion threshold is exceeded, and the user may set their preferences to generate an alarm when a second motion threshold is exceeded. In another example, the user 116 may set preferences to generate an alarm at the monitored property 102 when the pool device 104 detects motion.

In another example, the user 116 may set preferences to activate one or more lights in the vicinity of the pool 103 when the pool device detects motion during a specific time of the day. For example, the user may set their preferences to activate one or more lights in the vicinity of the pool 103 when the pool device 104 detects motion after 6:00 PM. In some implementations, the monitoring server 114 manages the monitoring system application. In some examples, when the electronic pool device 104 detects movement after a specific time, the control unit 112 prompts a speaker on the surface portion of the device to generate an audible alert. For example, when the device 104 detects motion after 6:00 PM, the control unit 112 generates an audible alert.

The electronic pool device 104 may also include a pH monitor, and one or more thermometers that monitor the pool conditions. The pH monitor may be located on an under surface of the surface portion of the device 104, and is configured to measure the pH of the pool water. In some examples, the pH monitor may be located on the camera portion of the electronic device 104. The user 116 may set one or more preferences for receiving notifications from the control unit 112 based on the measured pH readings. For example, the user 116 may set a preference to receive a notification when the pH exceeds a threshold value. The camera portion of the electronic device 104 includes a thermometer that measures the temperature of the pool water, and the surface portion of the device 104 includes a thermometer that measures the air temperature. The user 116 may set one or more preferences for receiving notifications from the control unit 112 based on the measured temperatures.

The electronic pool device 104 may monitor one or more other pool conditions. For example, the camera of the device 104 may detect debris at the bottom of the pool, and based on detecting the debris at the bottom of the pool, the control unit 112 communicates a notification to the user 116 indicating that maintenance is required. For another example, the camera of the device 104 may detect that the pool water is cloudy, and based on detecting the pool water is cloudy, the control unit 112 communicates a notification to the user 116 indicating that maintenance is required. In some implementations, the control unit 112 may periodically initiate communication with the electronic pool device 104. In the event that the electronic pool device 104 fails to respond to the communication initiated by the control unit 112, the control unit 112 may generate an alert to the user notifying the user that the electronic pool device 104 is offline. In some implementations, when the electronic pool device 104 fails to respond to the communication initiated by the control unit 112, the control unit 112 may initiate additional monitoring of the pool area. For example, the one or more cameras that have the pool 103 within their field of view may be powered on, and the captured video data is communicated to and analyzed by the control unit 112.

In other implementations, the electronic pool device 104 remains in the swimming pool 103 at all times. In these implementations, the camera portion of the electronic pool device 104 may include a sonar detector. The sonar detector is configured to detect objects under the surface of the water of the swimming pool 103. During a configuration stage, the sonar detector characterizes the underwater portion of the empty swimming pool 103. The sonar detector emits sound pulses and detects the sound pulses that are reflected off the surfaces of the swimming pool 103, and back to the sonar detector. The sonar detector generates a signature reflection pattern of the swimming pool 103 based on the data collected during configuration. The sonar detector is configured to detect when there is a change in the reflection pattern of the underwater profile of the pool 103, based on the reflection data received at the detector. When the sonar detector receives a reflection pattern that is different than the signature reflection pattern collected during configuration, the sonar detector determines an object entered the swimming pool 103.

The electronic pool device 104 communicates the sonar data to the control unit 112. The control unit 112 may implement one or more algorithms to determine whether the data detected by the sonar detector was caused by an object and not by other factors such as, weather or a vibration from the pool pump. During configuration, the system may be trained to rule out noise patterns that may cause the sonar detector to detect movement. When the control unit 112 determines the sonar data indicates the motion was caused by an object in the swimming pool 103 the control unit 112 generates a notification. The notification may be communicated to the user device 118 of the user 116 as an in-app notification.

In some implementations, the notification may include video data collected by the camera of the electronic pool device 104. When the sonar detector detects an object has entered the swimming pool 103, the camera may automatically begin to capture video data. The camera portion of the electronic device 104 may be positioned with an 180° field of view. The camera may be positioned so that each side surface of the swimming pool 103 is within the field of view of the camera. In some implementations, the swimming pool 103 may include one or more underwater cameras that are in communication with each other and in communication with the electronic pool device 104. The electronic pool device 104 may communicate the captured video data to the user device 118 of the user 116. The user 116 may review the captured data to determine whether the motion was caused by a person or pet in the pool 103, or whether the motion was caused by an object.

The user may indicate, through the monitoring system application, whether the motion was caused by a person or was caused by an object. For example, the user may review the video data and select a response indicating that the motion was caused by an object. The control unit 112 does not generate an alarm based on receiving data from the user 116 indicating the motion was caused by an object. The control unit may update the one or more motion thresholds based on the data received from the user indicating the motion was caused by an object.

When the user reviews the video data and selects a response indicating that the motion was by a person, the control unit 112 may generate an audible alarm at the monitoring property 102. The control unit 112 may communicate with an external server to dispatch authorities to the property 102 based on determining the user device 118 of the user is outside of a threshold distance from the property 102. For example, the control unit 112 may communicate directly with authority dispatch server. In other examples the control unit 112 communicates with the monitoring server 114 which in turn communicates with the authority dispatch server.

In some implementations, the surface portion of the electronic pool device 104 may include a switch that allows the user 116 to switch on the camera of the device 104. In these implementations, the user 116 may switch on the camera of the device 104 when the pool 103 is being utilized. When the pool 103 is being utilized the video data collected by the camera may be communicated to the control unit 112. The control unit 112 may be trained to identify data indicative of a swimmer in distress. During configuration of the electronic pool device 104, the control unit 112 may receive labeled data sets that teach the camera to identify a distressed swimmer. The user 116 may provide true or false responses based on reviewing video data of different actions in the captured video data. The user 116 may review the video data and the determinations made by the control unit 112 to respond whether each of the determinations was true or false. For example, the system may determine a person is swimming in the pool 103, and the user may confirm whether the person was swimming or was in distress.

In some implementations, when the in-home monitoring system is armed away, the control unit 112 assumes that the occupants of the monitored property 102 are away. The control unit 112 may confirm whether the property 102 is unoccupied by using one or more electronic devices and sensors located throughout the property 102. For example, the control unit 112 may switch on one or more cameras to scan the one or more rooms of the property to ensure the property is unoccupied. The control unit 112 may contact the authorities in response to detecting motion in the swimming pool of the monitored property 102. The control unit 112 may contact the authorities when the motion detected in the swimming pool exceeds a high motion threshold. The control unit may determine to contact the police department when the high motion threshold is exceeded when the homeowners are away from the property 102. In some implementations, when the high motion threshold is exceeded and the homeowners are away from the property 102, the control unit 112 may prompt the one or more cameras in the pool 103 vicinity to capture video data. The control unit 112 may use one or more video analytic techniques to determine whether the motion is caused by a human or an object. In some implementations, the control unit may be configured to perform facial recognition on the video data to identify the person detected in the swimming pool 103. In these implementations, the control unit 112 may generate one or more different notifications based on the identity of the person.

In some implementations, the swimming pool may be located at a property that is not monitored by a monitoring system. In these implementations, the pool device may communicate with an external monitoring server via cellular communication. The pool device may monitor for motion and communicate detected motion to the monitoring server.

Figure 2:
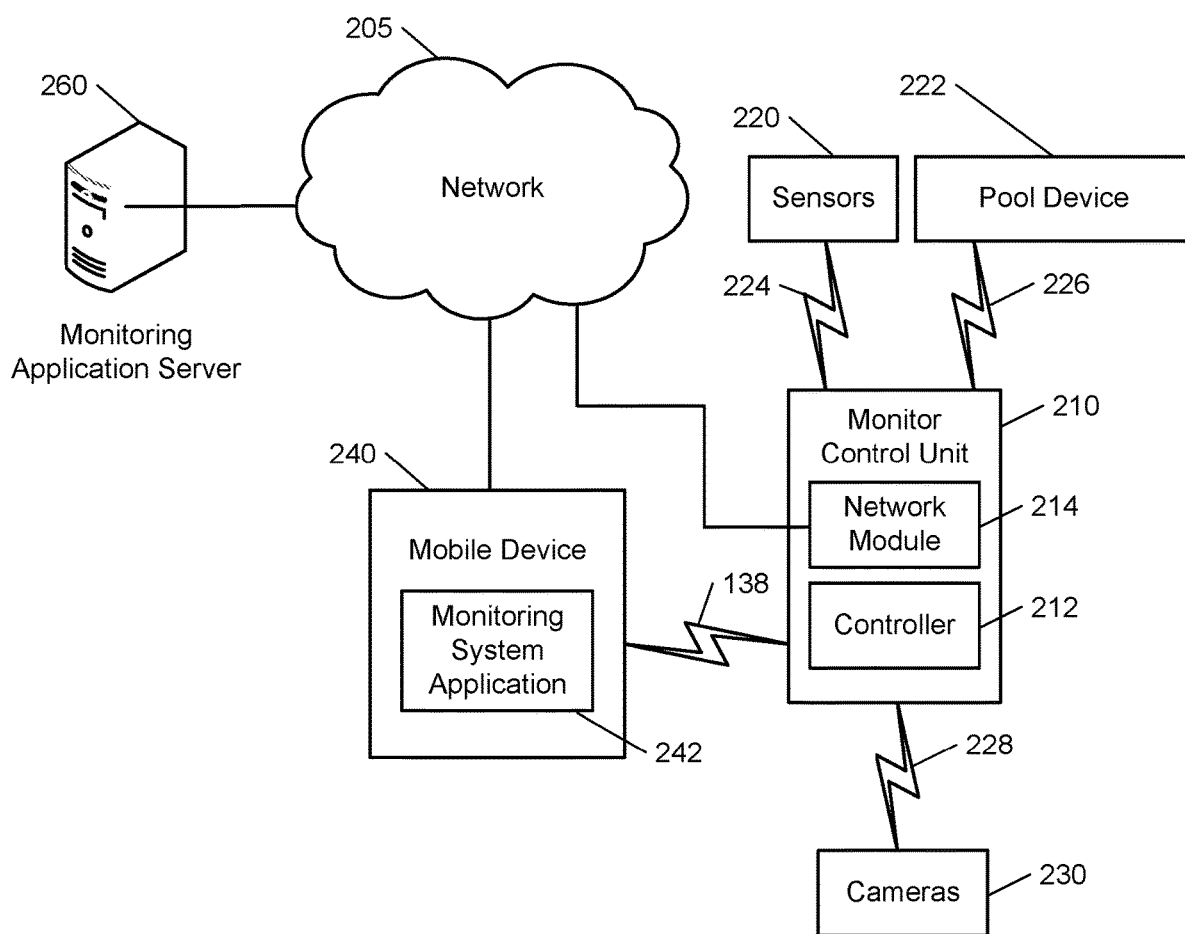
FIG. 2 illustrates an example of a monitoring system integrated with an electronic pool device.

FIG. 2 illustrates an example of a system 200 configured to monitor a property. The system 200 includes a network 205, a monitoring system control unit 210, one or more user devices 240, and a monitoring application server 260. The network 205 facilitates communications between the monitoring system control unit 210, the one or more user devices 240, and the monitoring application server 260. The network 205 is configured to enable exchange of electronic communications between devices connected to the network 205. For example, the network 205 may be configured to enable exchange of electronic communications between the monitoring system control unit 210, the one or more user devices 240, and the monitoring application server 260. The network 205 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 205 may include multiple networks or subnetworks, each of which may include, for example, a wired or wireless data pathway. The network 205 may include a circuit-switched network, a packet-switched data network, or any other network able to carry electronic communications (e.g., data or voice communications). For example, the network 205 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 205 may include one or more networks that include wireless data channels and wireless voice channels. The network 205 may be a wireless network, a broadband network, or a combination of networks including a wireless network and a broadband network.

The monitoring system control unit 210 includes a controller 212 and a network module 214. The controller 212 is configured to control a monitoring system (e.g., a home alarm or security system) that includes the monitor control unit 210. In some examples, the controller 212 may include a processor or other control circuitry configured to execute instructions of a program that controls operation of an alarm system. In these examples, the controller 212 may be configured to receive input from cameras, sensors, detectors, or other devices included in the alarm system and control operations of devices included in the alarm system or other household devices (e.g., a thermostat, an appliance, lights, etc.). For example, the controller 212 may be configured to control operation of the network module 214 included in the monitoring system control unit 210.

The network module 214 is a communication device configured to exchange communications over the network 205. The network module 214 may be a wireless communication module configured to exchange wireless communications over the network 205. For example, the network module 214 may be a wireless communication device configured to exchange communications over a wireless data channel and a wireless voice channel. In this example, the network module 214 may transmit alarm data over a wireless data channel and establish a two-way voice communication session over a wireless voice channel. The wireless communication device may include one or more of a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 214 also may be a wired communication module configured to exchange communications over the network 205 using a wired connection. For instance, the network module 214 may be a modem, a network interface card, or another type of network interface device. The network module 214 may be an Ethernet network card configured to enable the monitoring control unit 210 to communicate over a local area network and/or the Internet. The network module 214 also may be a voiceband modem configured to enable the alarm panel to communicate over the telephone lines of Plain Old Telephone Systems (POTS).

The monitoring system may include an electronic pool device 222 that is configured to monitor the swimming pool at monitored property. The electronic pool device 222 may be configured to communicate with the monitor control unit 210 through Bluetooth, Z-Wave, ZigBee, Wi-Fi, or other suitable form of wireless communication. The electronic pool device 222 may include a rechargeable battery that is powered by the energy generated by the water flowing through the plumbing system of the swimming pool. In some examples, the electronic device 222 may include a solar panel that is used to power the device.

The monitoring system may include multiple sensors 220. The sensors 220 may include a contact sensor, a motion sensor, a glass break sensor, or any other type of sensor included in an alarm system or security system. The sensors 220 also may include an environmental sensor, such as a temperature sensor, a water sensor, a rain sensor, a wind sensor, a light sensor, a smoke detector, a carbon monoxide detector, an air quality sensor, etc. The sensors 220 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the sensors 220 may include a radio-frequency identification (RFID) sensor that identifies a particular article that includes a pre-assigned RFID tag.

The one or more cameras 230 may be a video/photographic camera or other type of optical sensing device configured to capture images. For instance, the one or more cameras 230 may be configured to capture images of an area within a building monitored by the monitor control unit 210. The one or more cameras 230 may be configured to capture single, static images of the area and also video images of the area in which multiple images of the area are captured at a relatively high frequency (e.g., thirty images per second). The one or more cameras 230 may be controlled based on commands received from the monitor control unit 210.

The sensors 220, the pool device 222, and the cameras 230 communicate with the controller 212 over communication links 224, 226, and 228. The communication links 224, 226, and 228 may be a wired or wireless data pathway configured to transmit signals from the sensors 220, the pool device 222, and the cameras 230 to the controller 212. The communication link 224, 226, and 228 may include a local network, such as, 802.11 "Wi-Fi" wireless Ethernet (e.g., using low-power Wi-Fi chipsets), Z-Wave, Power Over Ethernet (POE), Zigbee, Bluetooth, "HomePlug" or other Powerline networks that operate over AC wiring, and a Category 5 (CAT5) or Category 6 (CAT6) wired Ethernet network.

The monitoring application server 260 is an electronic device configured to provide monitoring services by exchanging electronic communications with the monitor control unit 210, and the one or more user devices 240, over the network 205. For example, the monitoring application server 260 may be configured to monitor events (e.g., alarm events) generated by the monitor control unit 210. In this example, the monitoring application server 260 may exchange electronic communications with the network module 214 included in the monitoring system control unit 210 to receive information regarding events (e.g., alarm events) detected by the monitoring system control unit 210. The monitoring application server 260 also may receive information regarding events (e.g., alarm events) from the one or more user devices 240.

The one or more user devices 240 are devices that host and display user interfaces. The user device 240 may be a cellular phone or a non-cellular locally networked device with a display. The user device 240 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 240 may perform functions unrelated to the monitoring system, such as placing personal telephone calls, playing music, playing video, displaying pictures, browsing the Internet, maintaining an electronic calendar, etc.

The user device 240 includes a monitoring system application 242. The monitoring system application 242 refers to a software/firmware program running on the corresponding mobile device that enables the user interface and features described throughout. The user device 240 may load or install the monitoring system application 242 based on data received over a network or data received from local media. The monitoring system application 242 runs on mobile devices platforms, such as iPhone, iPod touch, Blackberry, Google Android, Windows Mobile, etc. The monitoring system application 242 enables the user device 240 to receive and process image and sensor data from the monitoring system.

In some implementations, the one or more user devices 240 communicate with and receive monitoring system data from the monitor control unit 210 using the communication link 228. For instance, the one or more user devices 240 may communicate with the monitor control unit 210 using various local wireless protocols such as Wi-Fi, Bolt, Lora, Bluetooth, Z-Wave, ZigBee, "HomePlug," or other Powerline networks that operate over AC wiring, or Power over Ethernet (POE), or wired protocols such as Ethernet and USB, to connect the one or more user devices 240 to local security and automation equipment. The one or more user devices 240 may connect locally to the monitoring system and its sensors and other devices. The local connection may improve the speed of status and control communications because communicating through the network 205 with a remote server (e.g., the monitoring application server 260) may be significantly slower.

Although the one or more user devices 240 are shown as communicating with the monitor control unit 210, the one or more user devices 240 may communicate directly with the sensors and other devices controlled by the monitor control unit 210. In some implementations, the one or more user devices 240 replace the monitoring system control unit 210 and perform the functions of the monitoring system control unit 210 for local monitoring and long range/offsite communication.

Figure 3:
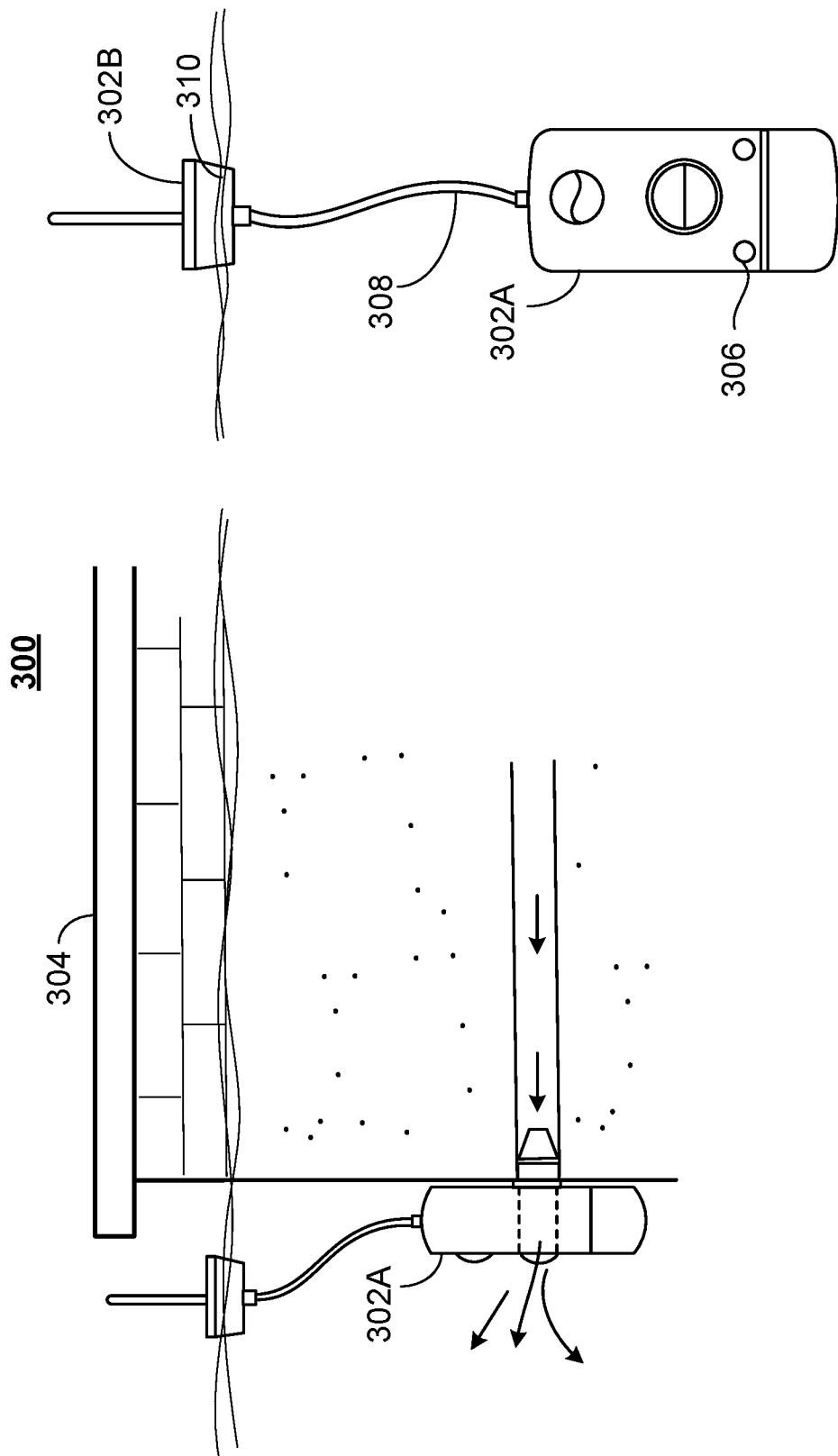
FIG. 3 illustrates an example of an electronic pool device.

FIG. 3 illustrates an example of an electronic pool device. For the implementation illustrated in FIG. 3, the electronic pool device may include a camera portion 302A and a surface portion 302B. The camera portion 302A is configured to be placed under the surface of the water, and may be mounted to an inlet of a pool jet. The pool water that flows through the pool jet may be used to power the battery of the camera portion 302A of the pool device 104. When the battery of the camera portion 302A of the pool device 104 is running low, the pool pump may increase the flow rate of the water through the one or more pool jets to increase the power supplied to the battery. In some implementations, the surface portion 302B may include a solar panel that converts solar energy to power the battery. The surface portion 302B of the electronic pool device is configured to float on the surface of the water of the pool 304. In some implementations, when the pool is in use and a swimmer contacts the surface portion of the pool device 104, the camera initiates the capture of video data.

The surface portion 302B may be attached to the camera portion 302A of the device by a flexible tether 308. In some examples, the tether may be configured to disconnect from the camera portion of the pool device 104 when the tether is under physical stress. The user may receive a notification through the monitoring system application when the control unit receives data from the pool device indicating that the tether disconnected. The surface portion 302B of the device may include an antenna 310 and one or more sensors. The antenna 310 is configured to allow the electronic pool device to communicate with the control unit 112 of the monitored property 102. The surface portion 302B may also include one or more sensors for detecting motion. The one or more motion detecting sensors may include an accelerometer, a gyroscope, a mercury switch, or any other appropriate motion detecting sensors. The surface portion 302B may also include may include a pH sensor, a thermometer, and a microphone.

The microphone on the surface portion 302B of the pool device 104 is a high-sensitivity microphone that is configured to detect an object that causes the pool water to thrash or splash sound when an object enters the pool. When the high-sensitivity microphone detects a splashing sound, the camera may switch on automatically to capture video data. In some implementations, the camera portion 302A of the pool device 104 may include the high sensitivity microphone.

Figure 4A:
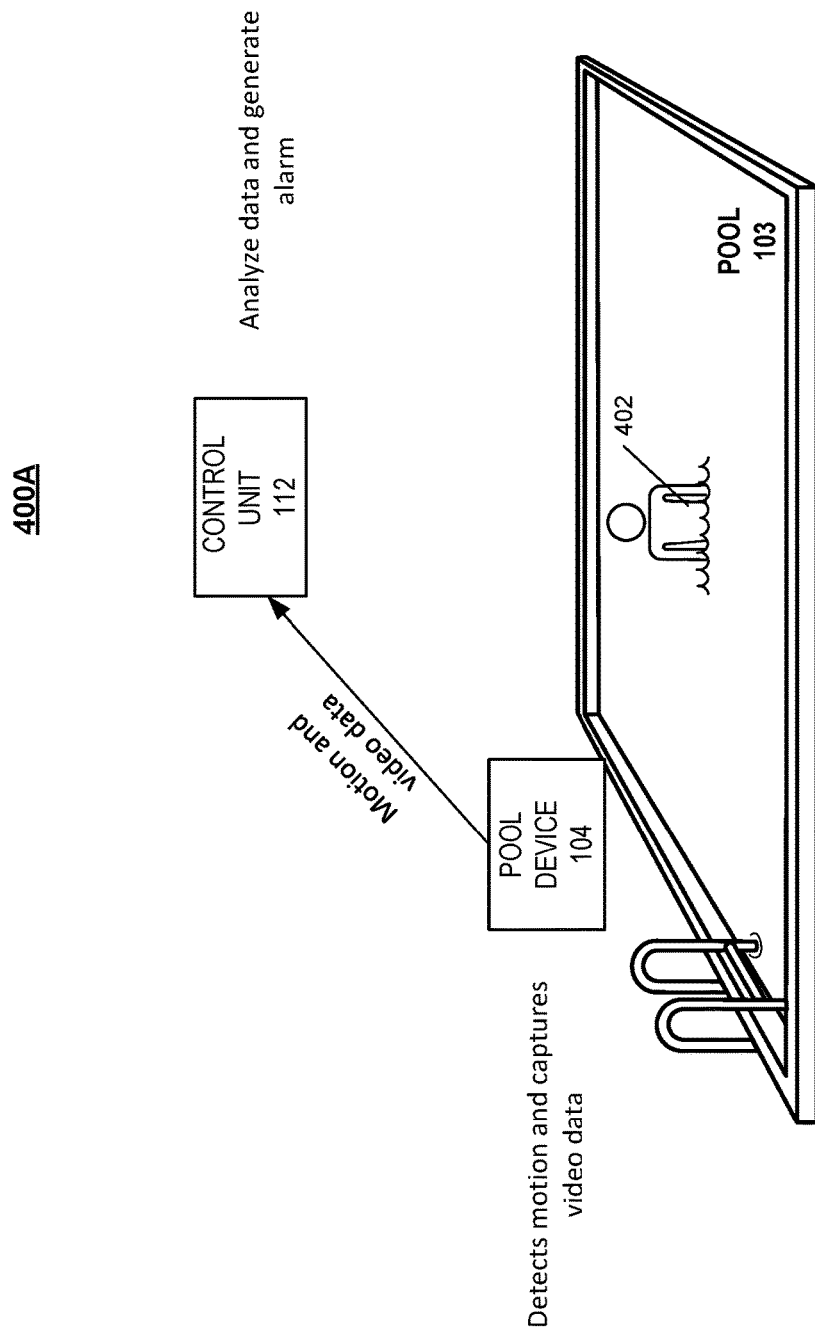
FIGS. 4A and 4B illustrate examples of a system for detecting motion in a swimming pool.
Figure 4B:
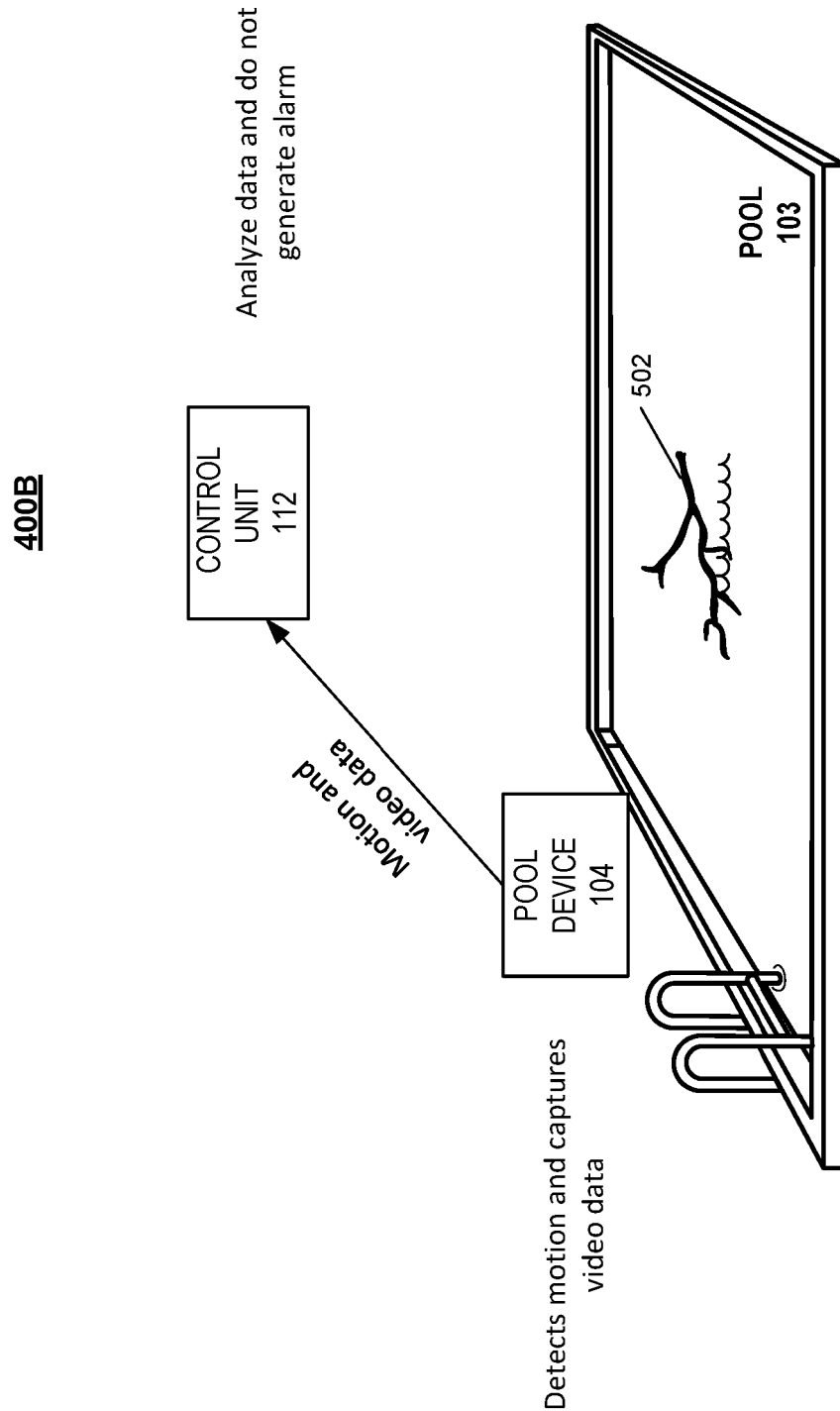

FIGS. 4A and 4B illustrate an example of a system for detecting motion in a swimming pool 103. As illustrated in FIGS. 4A and 4B, the pool device 104 detects motion in the pool 103, and communicates the motion data to the control unit 112. In the implementations where the electronic pool device 104 is placed in the swimming pool 103 when the pool is not being utilized, the one or more motion sensors of the surface portion of the pool device 104 detects motion in the pool 103 and communicates the motion data to the control unit 112. The control unit 112 compares the received motion data to a motion threshold, and based on the motion data exceeding the motion threshold, the control unit 112 communicates a notification to the user device of a resident of the monitored property. The control unit 112 simultaneously commands the camera of the pool device 104 to capture video data.

In the implementations where the electronic pool device 104 remains in the swimming pool 103 at all times, the camera portion of the pool device 104 includes a sonar detector. The sonar detector is configured to detect objects by detecting a change in the reflection pattern of the underwater profile of the swimming pool 103. When the sonar detector receives a reflection pattern that is different than the signature reflection pattern collected during configuration, the sonar detector determines an object entered the swimming pool 103. The pool device 104 communicates the sonar data to the control unit 112, and simultaneously begins to capture video data.

The video data captured by the pool device 104 is communicated to the control unit 112, and the control unit 112 analyzes the video data. The control unit 112 may be configured to use one or more techniques to analyze the video data. The control unit may analyze the data to determine whether the motion was caused by a person or by an object. In some implementations, the control unit may be configured to identify a swimmer in distress.

As illustrated in FIG. 4A, the control unit 112 analyzes the video data and determines that the motion is caused by a user 402. The control unit 112 may send a notification to a user device of a resident of the property, and the notification may include the video data captured by the control unit. The resident of the property may review the video data received. In some implementations, the control unit may be configured to perform facial recognition on the video data to identify the person detected in the swimming pool 103. The user may select an option to have the control unit generate an alarm based on determining that the user 402 in the swimming pool 103 seems to be a trespasser. In some implementations, the control unit 112 may automatically generate an audible alarm at the monitored property based on determining that the user 402 is an unknown user and the monitoring system at the property being armed away.

As illustrated in FIG. 4B, the control unit 112 analyzes the video data and determines that the motion is caused by a tree branch 502. The control unit 112 may send a notification to the user device of the resident of the property indicating that the motion was caused by an object. In these implementations, the control unit 112 does not generate an alarm.

Figure 5:
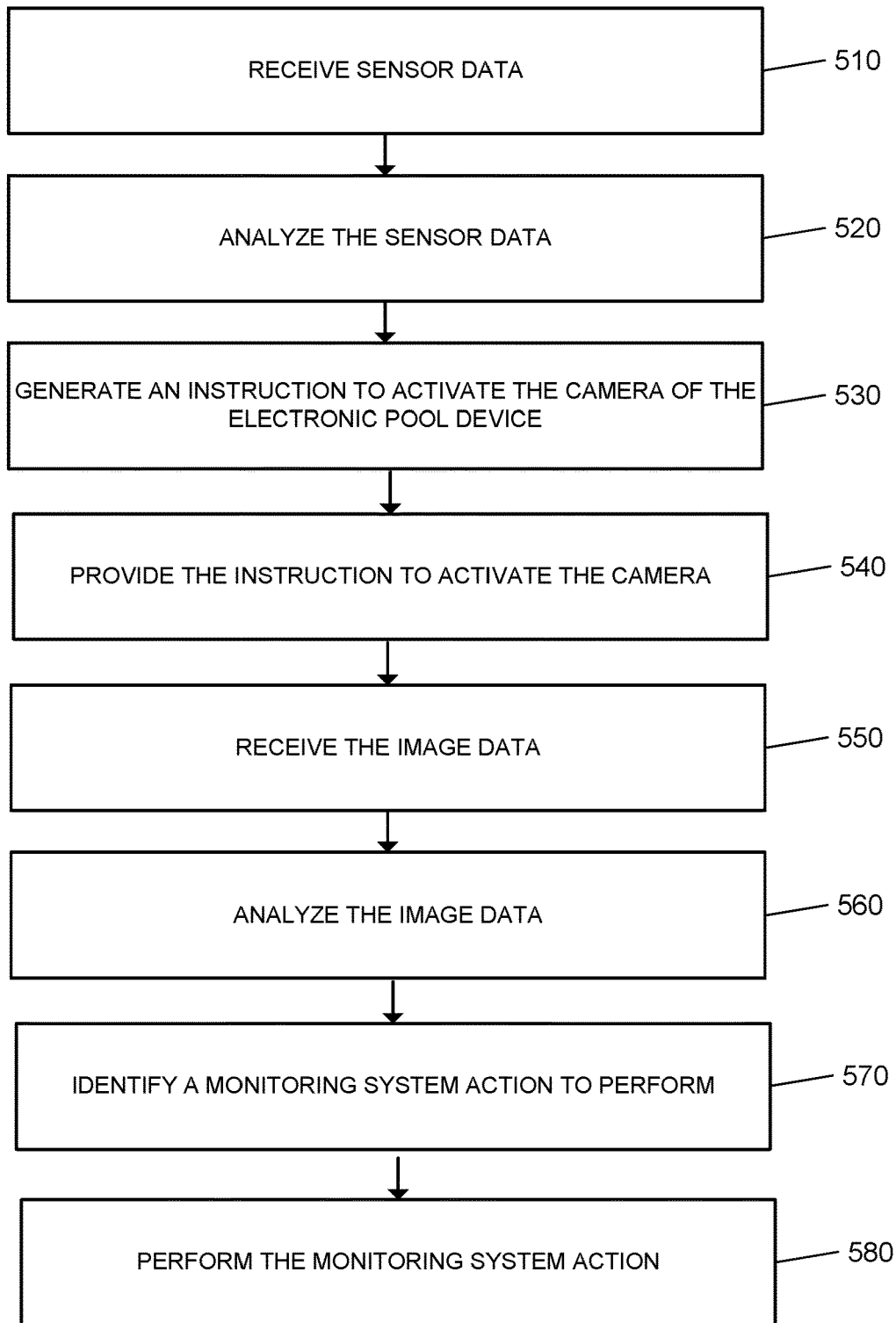
FIG. 5 is a flow chart of an example process for performing a monitoring system action

FIG. 5 is a flow chart of an example process for performing a monitoring system action. The monitoring system includes an electronic pool device 104 that is configured to monitor a swimming pool 103 that is located at the monitored property 102. The electronic pool device 104 includes a camera that is configured to capture video data and one or more sensors that are each configured to generate sensor data. The camera portion of the electronic pool device 104 may be placed under the surface of the water. The one or more sensors may be located at a surface portion of the electronic pool device 104. In some implementations, the one or more sensors may include an antenna, a microphone, an accelerometer, a gyroscope, a mercury switch, or any other appropriate motion detecting sensor.

The monitor control unit receives the sensor data from the electronic pool device (510). The antenna is configured to allow the electronic pool device 104 to communicate with the monitor control unit 112. In some implementations, the electronic pool device 104 may communicate with the monitor control unit 112 through Bluetooth, Z-Wave, Zig-Bee, Wi-Fi, or other suitable form of wireless communication. The electronic pool device 104 communicates sensor data to the monitor control unit 112 when at least one of the sensors detects a change. The one or more motion sensors may detect motion and communicate the motion data to the monitor control unit 112. In some implementations, the electronic pool device 104 may include a sonar detector. In these implementations, the monitor control unit 112 may receive sonar data from the electronic pool device 104 when the sonar detector detects an object in the pool 103.

The sonar detector may characterize the underwater portion of the swimming pool 103 during configuration. The sonar detector emits sound pulses and detects the sound pulses that are reflected off the surfaces of the swimming pool 103, and back to the sonar detector. The sonar detector generates a signature reflection pattern of the swimming pool 103 based on the data collected during configuration. The sonar detector is configured to detect when there is a change in the reflection pattern of the underwater profile of the pool 103, based on the reflection data received at the sonar detector. When the sonar detector receives a reflection pattern that is different than the signature reflection pattern collected during configuration, the sonar detector may determine that an object entered the swimming pool 103.

The monitor control unit analyzes the sensor data (520). The monitor control unit 112 may implement one or more algorithms to determine whether the sensor data received from the sonar detector was caused by an object in the pool 103, or was caused by other factors such as, weather or vibrations from the pool pump. During configuration of the electronic pool device 104, the monitor control unit 112 may be trained to identity and rule out noise patterns that may cause the sonar detector to detect movement.

The monitor control unit 112 may compare the motion data received from the one or more motion sensors to a motion threshold. The motion threshold may be determined by the monitor control unit 112. For example, the monitor control unit 112 may determine a motion threshold based on the current weather conditions at the monitored property 102. In these examples, the monitor control unit 112 may receive weather data from a weather data server 124. The monitor control unit 112 may adjust the motion threshold based on the weather data indicating windy or rainy conditions. For example, the monitor control unit 112 may increase the motion threshold in windy conditions.

In some implementations, the monitor control unit 112 adjusts the motion threshold based on the armed status of the property 102. In examples where the monitoring system at the monitored property 102 is armed away, the system assumes that the residents of the property are not at the property 102, and the monitor control unit 112 increases the motion threshold. In examples where the monitoring system is armed stay, the system assumes that the residents are at the property 102, and the monitor control unit 112 decreases the motion threshold. In examples where the monitoring system is unarmed, the system assumes that the residents are at the property 102, and the monitor control unit 112 decreases the motion threshold.

The monitor control unit 112 generates an instruction to activate the camera of the electronic pool device based on analyzing the sensor data (530). In response to determining an object or a person may be in the swimming pool 103, the monitor control unit 112 generates the instruction. The monitoring control unit 112 provides the instruction to activate the camera to the electronic pool device (540). The camera of the electronic pool device 104 initiates the capture of image data in response to receiving the instruction to activate from the monitor control unit 112. The monitor control unit 112 receives the image data from the camera of the electronic pool device (550). The electronic pool device may communicate electronically with the monitor control unit 112, and may communicate the one or more captured images to the monitor control unit 112.

The monitor control unit 112 analyzes the image data (560). The monitor control unit 112 may utilize one or more neural networks or one or more different machine learning techniques to analyze the image data received from the camera of the electronic pool device 104. The monitor control unit 112 may be configured to determine whether the motion is in the pool 103 was caused by a human or an object. In some implementations, the monitoring control unit 112 may be configured to determine whether the motion is caused by a pet. The monitor control unit 112 may be configured to utilize one or more analytic techniques to determine the actions of the person in the swimming pool 103. For example, the monitor control unit 112 may be configured to determine whether the person in the swimming pool 103 is swimming or the swimmer is in distress. In some implementations, the monitor control unit 112 may be configured count the number of laps that a swimmer swims while in the pool 103.

In some implementations, the swimming pool 103 may include one or more underwater cameras that are in communication with each other and in communication with the electronic pool device 104. The electronic pool device 104 may communicate the captured video data to the user device 118 of the user 116. The user 116 may review the captured data to determine whether the motion was caused by a person or pet in the pool 103, or whether the motion was caused by an object. The user may indicate, through the monitoring system application, whether the motion was caused by a person or was caused by an object. For example, the user may review the video data and select a response indicating that the motion was caused by an object. The control unit 112 does not generate an alarm based on receiving data from the user 116 indicating the motion was caused by an object. The control unit may update the one or more motion thresholds based on the data received from the user indicating the motion was caused by an object.

The monitor control unit identifies a monitoring system action to perform based on analyzing the image data (570). The monitor control unit 112 may identify an action to perform based on the determination made by the monitoring control unit 112. For example, when the monitor control unit 112 determines that the motion was caused by an object, the monitor control unit 112 may communicate a notification to the user device of the resident of the property. In some implementations, the user 116 may set one or more rules for the types of notifications generated by the monitor control unit 112. The user 116 may log into a monitoring system application that runs on the user device 118 and that is managed by the monitor control unit 112.

The monitor control unit 112 may sound an alarm at the property 102. For example, when the monitor control unit 112 determines that the monitoring system is armed away, and the monitored property is unoccupied, the monitor control unit 112 may generate an alarm at the property 102 when a person is detected in the pool 103. In these examples, when the monitor control unit 112 determines that the motion was caused by a person, the monitoring control unit 112 may communicate a notification to the user device of the resident of the property to determine whether to sound the alarm. In response to the resident indicating that the person in the pool is not authorized to be in the pool, the monitor control unit 112 may sound the audible alarm at the monitored property. The resident may indicate that the person in the swimming pool is not authorized, and that a voice commanding instructing the person to vacate the premises should be output by a speaker in the vicinity of the pool 103. In some examples, the monitor control unit 112 may prompt one or more lights in the vicinity of the pool to switch on based on the system detecting an unauthorized person in the pool 103.

The monitor control unit then performs the monitoring system action (580). The monitor control unit 112 may communicate the notification to the user device of the resident of the property, or may sound an alarm. In some examples, when the monitor control unit 112 determines that the person in the pool is distressed, the monitor control unit 112 may communicate a notification to the user device of the resident of the property, and simultaneously contact the relevant authorities to dispatch emergency personnel to the property 102.

In some implementations, the electronic pool device 104 may include a pH monitor, and one or more thermometers that are configured to monitor the pool conditions. The pH monitor may be located on an under surface of the surface portion of the electronic pool device 104. The pH monitor is configured to measure the pH of the pool water. The user 116 may set one or more preferences for receiving notifications from the control unit 112 based on the measured pH readings. For example, the user 116 may set a preference to receive a notification when the pH exceeds a threshold value. When the monitor control unit 112 receives pH data from the pH monitor, and determines that the pH exceeds the pH threshold, the monitor control unit 112 communicates a notification to the user device of the resident including the measured pH value, and indicating that maintenance is required.

In some implementations, the electronic pool device 104 includes a thermometer that is configured to measure the temperature of the pool water, and the surface portion of the device 104 includes a thermometer that is configured to measure the air temperature. The user 116 may set one or more preferences for receiving notifications from the monitor control unit 112 based on the measured temperatures. For example, the user may set a preference to receive a notification when the pool water exceeds 65 degrees. In some implementations, the electronic pool device 104 may monitor one or more other pool conditions. For example, the monitor control unit 112 may determine that there is debris at the bottom of the pool, and the monitor control unit 112 may communicate a notification to the user 116 indicating that maintenance is required.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

The invention claimed is:

1. A monitoring system that is configured to monitor a property, the monitoring system comprising:
   an electronic pool device that is configured to monitor a swimming pool located at the property, the electronic pool device including a camera that is configured to capture image data, and a sensor that is configured to generate sensor data; and
   a monitor control unit that is configured to:
   receive, from the electronic pool device, motion data;
   obtain weather data that indicates a weather condition at the property;
   based on obtaining the weather data, increase a motion threshold;
   analyze the motion data by comparing the motion data to the increased motion threshold;
   based on analyzing the motion data based on the weather condition, generate an instruction to activate the camera of the electronic pool device;
   provide, to the electronic pool device, the instruction to activate the camera;
   receive, from the electronic pool device, the image data;
   analyze the image data;
   based on analyzing the image data, identify a monitoring system action to perform; and
   perform the monitoring system action.

2. The system of claim 1, wherein:
   the motion data indicates a wave height and wave period of water in the swimming pool; and
   the monitor control unit is configured to:
   receive, from a server, the weather data, wherein the weather condition at the property comprises a wind forecast at the property;
   based on the weather data, adjust a wave height threshold and a wave period threshold; and
   analyze the motion data by comparing the motion data that indicates the wave height and the wave period to the wave height threshold and the wave period threshold.

3. The system of claim 1, wherein the monitor control unit is configured to:
   receive first historical sensor data captured by the electronic pool device and other electronic pool devices during emergency events;
   receive second historical sensor data captured by the electronic pool device and the other electronic pool devices during non-emergency events; and
   train, using machine learning, a model that is configured to receive the sensor data and determine whether an emergency event likely exists.

4. The system of claim 3, wherein the monitor control unit is configured to:
   analyze the sensor data by providing the sensor data as an input to the model that is configured to receive the sensor data and determine whether the emergency event likely exists; and
   generate the instruction to activate the camera of the electronic pool device based on determining that the emergency event likely exists.

5. The system of claim 1, wherein the monitor control unit is configured to:
   determine that an armed status of the monitoring system is armed away;
   based on determining the armed status of the monitoring system is armed away, increase the motion threshold; and
   analyze the motion data by comparing the motion data to the increased motion threshold.

6. The system of claim 1, wherein the monitor control unit is configured to:
   determine an armed status of the monitoring system;
   based on determining the armed status, increase the motion threshold; and
   analyze the motion data by comparing the motion data to the increased motion threshold.

7. The system of claim 1, wherein the monitor control unit is configured to:
   determine an armed status of the monitoring system;
   based on determining the armed status, decrease the motion threshold; and
   analyze the motion data by comparing the motion data to the decreased motion threshold.

8. The system of claim 1, wherein the monitor control unit is configured to:
   determine that use of the pool is not allowed at a current time;
   analyze the image data by analyzing the image data using one or more video analytic techniques;
   based on analyzing the image data using the one or more video analytic techniques, determine that a person is in the pool;
   based on determining that the person is in the pool at the current time when the use of the pool is not allowed, identify the monitoring system action to perform by identifying a monitoring system action of activating an alarm; and
   perform the monitoring system action of activating the alarm by activating the alarm.

9. The system of claim 8, wherein the monitor control unit is configured to:
   identify the monitoring system action to perform by identifying a monitoring system action of activating one or more lights in a vicinity of the pool; and
   perform the monitoring system action by activating the one or more lights in the vicinity of the pool.

10. The system of claim 1, wherein the monitor control unit is configured to:
    based on analyzing the image data, determine that an object is at the bottom of the pool;
    based on determining that the object is at the bottom of the pool, identify the monitoring system action to perform by identifying the monitoring system action of communicating a notification to a user device of a resident of the property; and
    perform the monitoring system action by communicating the notification to the user device of the resident of the property indicating that maintenance is required.

11. The system of claim 1, wherein the monitor control unit is configured to:
    based on analyzing the motion data, the weather data, and the image data, determine that a person in the pool is in distress;
    based on determining that the person in the pool is in distress, identify the monitoring system action to perform by identifying a monitoring system action of contacting emergency services; and
    perform the monitoring system action by contacting emergency services.

12. The system of claim 1, wherein the monitor control unit is configured to:

receive, from the electronic pool device, pH data, wherein the electronic pool device includes a pH sensor that is configured to measure a pH of water in the swimming pool;
analyzing the pH data by comparing the pH data to a pH threshold;
based on comparing the pH data to the pH threshold, determine that the pH data exceeds the pH threshold; and
based on determining that the pH data exceeds the pH threshold, perform a monitoring system action by communicating a notification to a user device of a resident of the property.

13. The system of claim 1, wherein the electronic pool device comprises:
a first portion that is located under a pool water surface, the first portion including one or more cameras and one or more sensors;
a second portion that is located above the pool water surface, the second portion including one or more motion sensors; and
the first portion is connected to the second portion by a flexible tether.

14. The system of claim 13, wherein the first portion of the electronic pool device that is located under the pool water surface includes a sonar detector.

15. A computer implemented method comprising:
receiving, by a monitoring system that is configured to monitor a property and from an electronic pool device that is configured to monitor a swimming pool at the property, motion data;
obtaining, by the monitoring system, weather data that indicates a weather condition at the property;
based on obtaining the weather data, increasing, by the monitoring system, a motion threshold;
analyzing, by the monitoring system, the motion data by comparing the motion data to the increased motion threshold;
based on analyzing the motion data based on the weather condition, generating, by the monitoring system, an instruction to activate a camera of the electronic pool device;
providing, by the monitoring system to the electronic pool device, the instruction to activate the camera;
receiving, by the monitoring system from the electronic pool device, image data;
analyzing, by the monitoring system, the image data;
based on analyzing the image data, identifying a monitoring system action to perform; and
performing the monitoring system action.

16. The method of claim 15, comprising:
receiving the motion data that indicates a wave height and wave period of water in the swimming pool;
receiving, from a server, the weather data, wherein the weather condition at the property comprises a wind forecast at the property;
based on the weather data, adjusting a wave height threshold and a wave period threshold; and
analyzing the motion data by comparing the motion data that indicates the wave height and the wave period to the wave height threshold and the wave period threshold.

17. The method of claim 15, comprising:
receive first historical sensor data captured by the electronic pool device and other electronic pool devices during emergency events;
receive second historical sensor data captured by the electronic pool device and the other electronic pool devices during non-emergency events; and
train, using machine learning, a model that is configured to receive the sensor data and determine whether an emergency event likely exists.

18. The method of claim 17, comprising:
analyzing the sensor data by providing the sensor data as an input to the model that is configured to receive the sensor data and determine whether the emergency event likely exists; and
generating the instruction to activate the camera of the electronic pool device based on determining that the emergency event likely exists.

19. The system of claim 1, wherein the electronic pool device comprises:
a rechargeable battery that is charged, at least in part, by energy generated from water flowing within the swimming pool.

* * * * *